(12) United States Patent
Fujisawa et al.

(10) Patent No.: US 7,342,491 B2
(45) Date of Patent: Mar. 11, 2008

(54) HUMAN BODY MONITORING SYSTEM

(75) Inventors: Tomonori Fujisawa, Shinagawa-ku (JP); Shouji Satou, Nasushiobara (JP)

(73) Assignee: Kabushiki Kaisha Eighting, Tokyo (JP)

( * ) Notice: Subject to any disclaimer, the term of this patent is extended or adjusted under 35 U.S.C. 154(b) by 35 days.

(21) Appl. No.: 10/586,252

(22) PCT Filed: Jan. 18, 2005

(86) PCT No.: PCT/JP2005/000547

§ 371 (c)(1),
(2), (4) Date: Jul. 17, 2006

(87) PCT Pub. No.: WO2005/069244

PCT Pub. Date: Jul. 28, 2005

(65) Prior Publication Data

US 2007/0252708 A1 Nov. 1, 2007

(30) Foreign Application Priority Data

Jan. 19, 2004 (JP) .............................. 2004-009990

(51) Int. Cl.
*G08B 1/08* (2006.01)

(52) U.S. Cl. ........................... 340/539.12; 340/310.06; 340/436; 340/825.69; 340/539.13; 455/517; 600/300

(58) Field of Classification Search ........... 340/539.12, 340/435, 436, 446, 454, 621, 657, 825.69, 340/310.06, 311.1, 447, 448; 455/517, 550.1, 455/500, 507

See application file for complete search history.

(56) References Cited

U.S. PATENT DOCUMENTS

| | | | |
|---|---|---|---|
| 5,173,660 A * | 12/1992 | Marsden | 324/248 |
| 5,239,265 A * | 8/1993 | Sugahara | 324/309 |
| 5,265,609 A * | 11/1993 | Buchanan et al. | 600/409 |
| 5,311,867 A | 5/1994 | Kynor | |
| 5,615,210 A * | 3/1997 | Kaiyama et al. | 370/389 |
| 5,839,077 A * | 11/1998 | Kowaguchi | 455/517 |
| 5,857,144 A * | 1/1999 | Mangum et al. | 455/11.1 |
| 6,023,633 A * | 2/2000 | Kado | 600/409 |

(Continued)

FOREIGN PATENT DOCUMENTS

JP H06-277190 10/1994

(Continued)

*Primary Examiner*—Benjamin C. Lee
*Assistant Examiner*—Daniel Previl
(74) *Attorney, Agent, or Firm*—Manabu Kanesaka (57) ABSTRACT

The present invention provides a human body monitoring system capable of monitoring a human body by checking various parameters and also reporting health impairment such as sudden illness and emergency such as a crime to a prespecified contact address. A monitoring device carried by an object person for monitoring and having a transmitting section and a mobile terminal carried by the object person for monitoring and having a receiving section are connected in a wireless system using weak electric wave. An abnormal signal and positional information are set to the prespecified contact address or a management center based on the abnormal data signal received by the mobile terminal from the monitoring device. The monitoring device includes a non-contact type biomagnetic field measuring sensor for measuring a trend of action potential in the object person and transmits the abnormal data signal to the mobile terminal. The coverage distance of the weak electric wave is within 10 meters.

5 Claims, 5 Drawing Sheets

U.S. PATENT DOCUMENTS

| | | | |
|---|---|---|---|
| 6,208,884 B1 * | 3/2001 | Kumar et al. | 600/409 |
| 6,369,337 B1 * | 4/2002 | Machiyama et al. | 177/25.13 |
| 6,470,220 B1 * | 10/2002 | Kraus et al. | 607/103 |
| 6,520,903 B1 * | 2/2003 | Yamashiro | 600/9 |
| 2001/0012761 A1 * | 8/2001 | Mitama et al. | 455/41 |
| 2005/0114170 A1 * | 5/2005 | Park et al. | 705/2 |

FOREIGN PATENT DOCUMENTS

| | | |
|---|---|---|
| JP | H07-311622 | 11/1995 |
| JP | H11-284711 | 10/1999 |
| JP | 2000-262480 | 9/2000 |
| JP | 2001-112725 | 4/2001 |
| JP | 2001-236583 | 8/2001 |
| JP | 2001-348176 * | 11/2001 |
| JP | 2002-261955 | 9/2002 |
| JP | 2003-087436 | 3/2003 |
| JP | 2003-109160 | 4/2003 |
| JP | 2003-111735 | 4/2003 |
| JP | 2003-125097 | 4/2003 |
| JP | 2003-141667 | 5/2003 |
| JP | 2003-150718 | 5/2003 |
| JP | 2003-218997 | 7/2003 |
| JP | 2003-219062 | 7/2003 |
| JP | 2003-298756 | 10/2003 |

* cited by examiner

HUMAN BODY MONITORING SYSTEM

TECHNICAL FIELD

The present invention relates to a human body monitoring system for measuring and monitoring an action potential generated from organs, muscles or the like in a living body with a biomagnetic field measurement sensor and also for reporting a result of the measurement via a mobile terminal or the like as a medium to a prespecified point of contact or a management center.

BACKGROUND ART

In association with rapid popularization and spreading of mobile telephones, there have been proposed a health management and abnormality reporting system making use of a mobile terminal and a living body sensor.

For instance, Japanese Patent Laid-Open Publication No. 2003-150718 (Patent document 1) discloses an always-connected health-management system a portable remote health condition data measuring device in which a notebook type health condition data measuring device and a commercially available mobile terminal are combined with each other and a management center for collecting and analyzing data transmitted from the measuring device. In the invention, however, the living body sensor is required to be directly contacted to a skin of a living body, and medical knowledge is more or less required for determine a position where the sensor is to be set, and therefore the system is very hard to use for users.

Japanese Patent Laid-Open Publication No. 2003-125097 (Patent document 2) discloses a health information collecting device for mobile terminals for the purpose to collect health information with a mobile terminal, but the invention is novel only in the point that a signal transmission path between a living body sensor and a mobile terminal as a communication medium is wireless, and in the point that a health database system is linked to the device.

Japanese Patent Laid-Open Publication No. 2002-261955 (Patent document 3) discloses a system set in an accessory such as a wrist watch or a necklace and including not only a sensor for measuring a blood pressure and a body temperature, but also a transmission circuit for transmitting a radio signal when an emergency is to be reported. With this system, when it is determined that a user's health condition is not good by a microcomputer in the accessory, a radio signal is transmitted from the transmission circuit to notify occurrence of the emergency to a prespecified place such as the user's home or a place where the user has gone. However, novelty of the invention consists only in the point that a frequency of 2.45 GHz is used for transmission of a radio signal to suppress the influence to other medical equipment caused by a malfunction.

Japanese Patent Laid-Open Publication No. 2003-109160 (Patent document 4) describes that a living body sensor is attached to a human body to detect an attack of a cardiac disease, data acquired by the sensor is sent from the sensor to a mobile terminal from time to time, and a report on an emergency is made based on the data.

Japanese Patent Laid-Open Publication No. 2003-141667 (Patent document 5) describes a method of reporting an abnormal health condition of an inhabitant in a solitary home, a home of a few members, and especially in a home of the aged person or aged people by detecting the abnormal health condition with a water meter, a gas meter, and other types of sensors and reporting the abnormal condition to people responsible to checking the meters, a security center, and related people. The invention utilizes living information such as displays of a water meter or a gas meter, and this system is adapted only to use in a house, and is a typical example lacking versatility.

As an invention not using an external device such as a living body sensor, Japanese Patent Laid-Open Publication No. 2003-87436 (Patent document 6) describes an emergency reporting system enabling registration in an emergency reporting system and up to transmission of information on an emergency without using any voice and an emergency reporting device used in the system, and furthermore Japanese Patent Laid-Open Publication No. 2003-111735 (Patent document 7) describes an health information management system utilizing a portable terminal device such as a mobile terminal, a PHS (registered trade name). In the two inventions described above, a user having an abnormal health condition is required to act for operating a mobile terminal, and therefore the inventions lack the usefulness in practical use as a system for reporting an emergency in a human health condition.

Japanese Patent Laid-Open Publication No. HEI 11-284711 (Patent document 8) describes a mobile terminal having a crime prevention bell buzzer function as a crime prevention alarm device and a reporting system. It is generally considered that, when a perpetrator tries to do harm such as restraint to a victim, at first the perpetrator holds both arms of the victim, and the victim can not pull a hand strap as expected in the invention.

Furthermore there have been proposed a crime prevention alarming device and a reporting system based on a combination of living body abnormality adaptors, and for instance, Japanese Patent Laid-Open Publication No. 2003-218997 (Patent document 9) describes a mobile terminal having both a crime prevention function and an emergency alerting function and a method of operating the crime prevention function and the emergency alerting function. With the action such as pulling out an antenna with a pulling force stronger than a prespecified level or pressing any key, the invention is rather low in the effectiveness and can hardly be carried out.

Japanese Patent Laid-Open Publication No. 2003-219062 (Patent document 10) describes a mobile terminal having a crime prevention function for alerting occurrence of an emergency and a crime prevention adaptor for a mobile terminal. It can not be regarded, however, that the device according to the invention is adapted for reporting an emergency.

Japanese Patent Laid-Open Publication No. 2001-236583 (Patent document 11) discloses a safety confirmation device in which information concerning safety of an object person is collected with a sensor and the information is accumulated as time history record, a degree of abnormality is determined by an abnormality degree classifying section, the data is reported to a reporting unit with a prespecified small power wireless communication, and then the information is delivered from the reporting unit to an external device. However, in the safety confirmation device, data collected by spending a long time is required to determine a degree of "abnormality", and the device is not adapted for a case requiring a quick countermeasure to an emergency.

Patent document 1: Japanese Patent Laid-Open Publication No. 2003-150718
Patent document 2: Japanese Patent Laid-Open Publication No. 2003-125097
Patent document 3: Japanese Patent Laid-Open Publication No. 2002-261955

Patent document 4: Japanese Patent Laid-Open Publication No. 2003-109160
Patent document 5: Japanese Patent Laid-Open Publication No. 2003-141667
Patent document 6: Japanese Patent Laid-Open Publication No. 2003-87436
Patent document 7: Japanese Patent Laid-Open Publication No. 2003-111735
Patent document 8: Japanese Patent Laid-Open Publication No. HEI 11-284711
Patent document 9: Japanese Patent Laid-Open Publication No. 2003-218997
Patent document 10: Japanese Patent Laid-Open Publication No. 2003-219062
Patent document 11: Japanese Patent Laid-Open Publication No. 2001-236583

DISCLOSURE OF INVENTION

The present invention was made, based on the long term strenuous researches and studies, to solve the problems described above, and an object of the present invention is to provide a human body monitoring system capable of monitoring in a wide area which is equivalent to a coverage area of a mobile terminal and measuring and monitoring action potentials as a sensor sensing and reporting occurrence of an emergency such as an acute disease and a crime, and also capable of reporting occurrence of the emergency to a prespecified contact address or a management center without requiring any specific action by a user.

The present invention provides a human body monitoring system including a monitoring device carried by a person to be monitored and having a transmitting section and a mobile terminal carried by the person to be monitored and having a receiving section. In the human body monitoring system, the mobile terminal is connected to the monitoring device through a wireless communication system using a weak electric wave and is capable of reporting, based on an abnormal data signal received by the mobile terminal from the monitoring device, the abnormal signal and information concerning a position where an emergency occurs to a prespecified contact address or a management center, and the monitoring device has a non-contact biomagnetic field measuring sensor, monitors trends in action potentials in the target person for monitoring with the sensor, and transmits the abnormal data signal to the mobile terminal.

A coverage distance of the weak electric wave is within 10 meters, and more preferably within a range from several meters up to 10 meters.

The monitoring device preferably includes an action potential measuring section comprising the biomagnetic field measuring sensor; a trend data converting section for converting information concerning the action potentials to digital data in the chronological order; a data accumulating section for serially accumulating the trend data; a data determining section for determining whether accumulated data is normal or abnormal; a pattern analyzing section for determining whether a continuous pattern of action potential trend data groups determined as abnormal by the data determining section is abnormal or not; a transmitting section for transmitting a signal classifying and indicating a degree of abnormality determined as abnormal by the pattern analyzing section to the mobile terminal; a fixed time signal generating section for generating a connection confirmation signal irrespective of a result of determination by the pattern analyzing section; and a control section for controlling each of the sections above.

The monitoring device preferably includes an action potential measuring section comprising the biomagnetic field measuring sensor; a trend data converting section for converting information concerning the action potentials to digital data in the chronological order; a data accumulating section for serially accumulating the trend data; a data determining section for determining whether accumulated data is normal or abnormal; a transmitting section for transmitting a signal classifying and indicating a degree of abnormality determined as abnormal by the data determining section to the mobile terminal; a fixed time signal generating section for generating a connection confirmation signal irrespective of a result of determination by the data determining section; and a control section for controlling each of the sections above.

The mobile terminal preferably includes a received signal analyzing section for analyzing an abnormal data signal received by the receiving section and notifying a result of the analysis to a control section of the mobile terminal.

When the biomagnetic field measuring sensor according to the present invention is employed as a monitoring section, a non-contact monitoring section can be realized, so that inconvenience or discomfort to a person to be monitored can be dissolved. An action potential measured by the biomagnetic field measuring sensor is generated in a medically excited state of a human body and changes at an order of milliseconds (msec), so that the action potential can be determined within a short period of time. Therefore measurement of action potentials is effective not only to detect occurrence of an accidental emergency such as an acute disease, but also to detect such crimes as hostage-taking, abduction, violence, or the equivalent. Because of the features, the biomagnetic field sensor according to the present invention can be applied in a wide area to detection of an emergency associated with an excitation in a human body.

Especially, since no specific action of a person to be monitored is required in the present invention, occurrence of an emergency can be reported to a third party without being noticed by a perpetrator, so that the effectiveness is quite high.

Furthermore, since a function for transmitting positional information together with information concerning occurrence of an emergency is employed, the present invention enables detection of a place where a person to be monitored is present within a short period of time, and is effective for both health management and crime prevention.

Even when the mobile terminal as a communication medium is separated from the monitoring device, occurrence of an emergency is reported. Therefore, even when the monitoring device is junked or broken, the effectiveness or usefulness in practical use is extremely high.

10: Person to be monitored
11: Monitoring device
12: Mobile terminal
13: Contact address or management center
14: GPS
20: Control section for monitoring device
21: Active potential measuring section
22: Trend data converting section
23: Data accumulating section
24: Data analyzing section
25: Pattern analyzing section
26: Transmitting section
27: Fixed time signal generating section
31: Receiving section of mobile terminal
32: Received signal analyzing section

BEST MODE FOR CARRYING OUT THE INVENTION

Many researches have been made for bioelectricity since discovery of the convulsion phenomenon in muscle of a frog's leg caused by lighting discharge in $18^{th}$ century by Galvani in Italy. The electrocardiogram, electromyogram, brain wave and the like actively utilized at sites of medical treatment are prepared by measuring a current flowing in various portions of a human body with various sensors directly set on a human skin.

Electric phenomena are never disassociated from magnetic phenomena, but researches on the magnetic phenomena are not so active. One of reasons is that a magnetic field generated in a human body is extremely weak. However, after appearance of the Josephson junction device which is a device for a computer developed in 1960s, and furthermore in association with development of superconductive quantum interference device (SQUID) or the like, now measurement of action potentials in a living body with a non-contact type device is possible.

Cells of nerves and muscles constituting a living body are easily excited, and the cells do not generate electricity when the living body lives quietly without any excitation (resting state), but when any stimulus is added and the living body is excited (excited state), the cells generate electricity. The electricity generated in the state is called action potential or ion pulse. This action potential changes by time unit of msec, and a principle of the present invention is to measure the action potential with a biomagnetic sensor such as a superconductive quantum interference device (SQUID) within a short period of time for the purpose to detect any abnormality in a human body.

The reason why the living body sensor such as a superconductive quantum interference device (SQUID) is used for measurement of the action potential is to realize a non-contact type living body sensor which, different from the contact type sensors such as electrocardiogram, electromyogram, brain wave, does not give any discomfort to a subject to be monitored. Advantages of the use of a biomagnetic sensor are described below with reference to FIG. 5.

Figure 5:
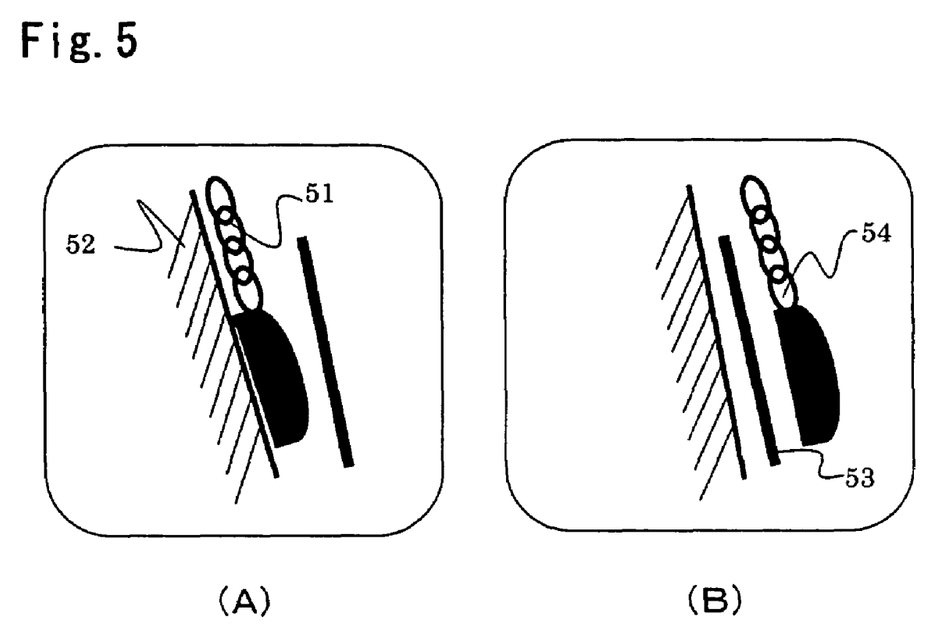
FIG. 5 is a side cross-sectional view illustrating a sensor mounted portion for comparison of the present invention to the prior art.

FIG. 5 is a cross-sectional view illustrating a sensor mounted portion viewed from the side, and in the case of the conventional sensor shown in FIG. 5(A), a contact type living body sensor 51 used, for instance, in Patent document 1 described above, is closely attached to a surface 52 (skin) of a body. In the case of the sensor according to the present invention shown in FIG. 5(B), a non-contact type sensor 54 is mounted on a dress 53. In other words, when using the conventional type of living body sensor 51, the living body sensor 51 is closely attached and is sometimes fixed to a human body with adhesive tape or the like to skin for measuring pulse, cardiac beat, blood pressure, and body temperature. In the present invention, it is not necessary to attach or fix a sensor to a human body, and the living body sensor 54 according to the present invention can be mounted on a human body quite easily.

Figure 1:
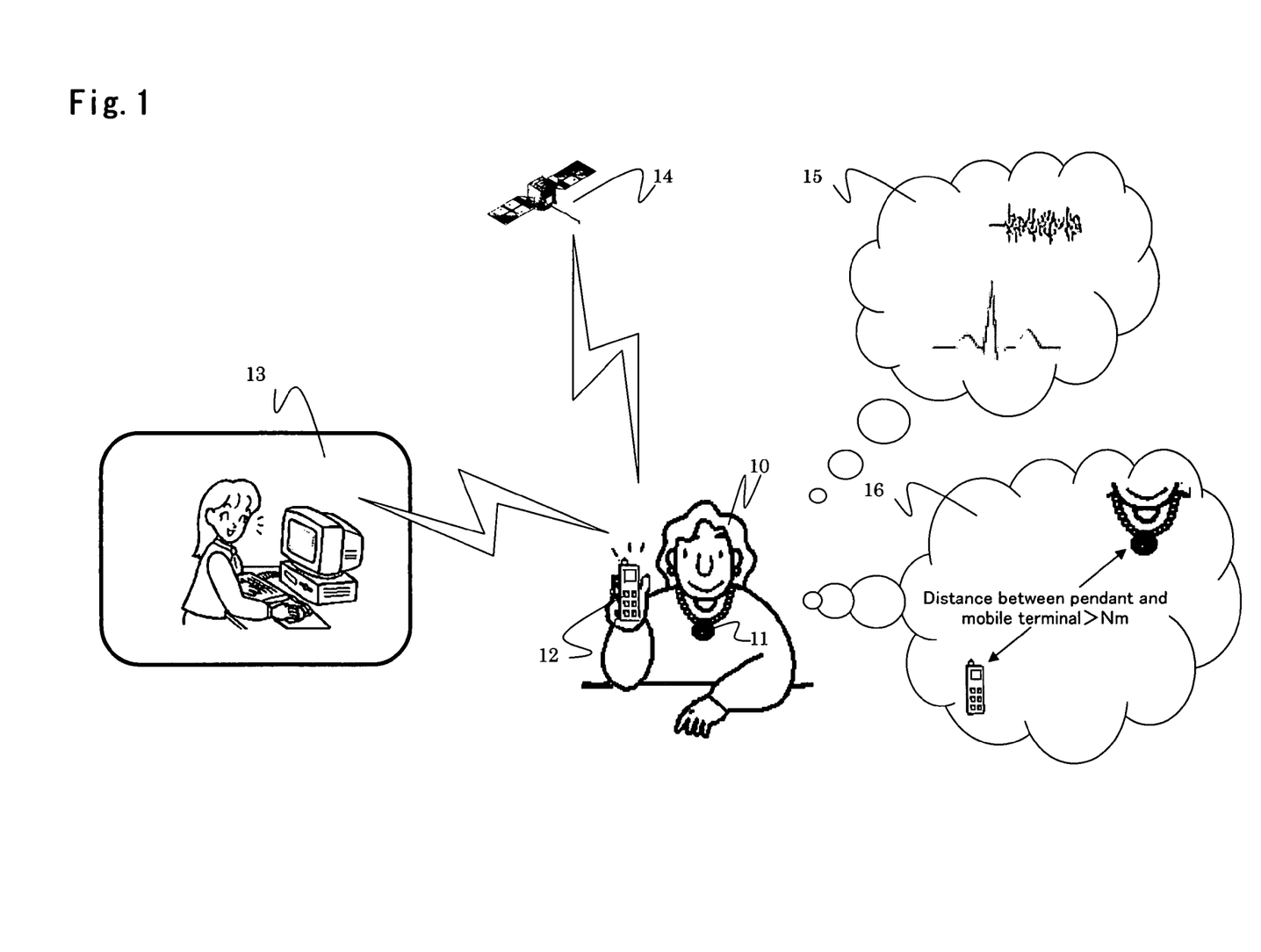
FIG. 1 is a general concept view illustrating a human body monitoring system according to the present invention.

FIG. 1 is a general concept view illustrating a human body monitoring system according to the present invention, and an object person 10 for monitoring wears a pendant type monitoring device 11 on his or her body, and also carried a mobile terminal 12 such as a mobile a cellular telephone. The monitoring device 11 has a non-contact type biomagnetic field measuring sensor, and the sensor measures a trend in action potential of a living body and transmits abnormal data signal to the mobile terminal 12, while the mobile terminal 12 sends an abnormal signal to a prespecified contact address or to a management center 13 based on the received abnormal data signal. In this step, also positional information acquired by the GPS 14 may be attached to the abnormal signal and furthermore a signal telling the current position may be transmitted together with the abnormal signal.

In FIG. 1, a balloon 15 is a waveform chart showing action potentials which can be measured from organs or muscles of a living body. A balloon 16 illustrates the situation in which, when a distance between a pendant as the monitoring device 11 and the mobile terminal 12 is over a prespecified distance N m, the mobile terminal 12 automatically reports the abnormality and transmits a signal concerning the current position.

A form of the monitoring device 11 is not always limited to a pendant, and various forms may be employed including those of an armlet, a wrist watch, a pocket watch, a notebook, a pen or a pencil, a card which can be put in a pocket or the like. Furthermore, forms such as a shoulder bag or accessories may be employed so long as an appropriate distance from the object person 10 for monitoring can be maintained.

Furthermore, as described later with reference to FIG. 4, a transmitting section 26 of the monitoring device 11 is preferably a transmitter transmitting an extremely weak electric wave with a coverage distance of 10 meters or less, especially several meters up to 10 meters is preferable so that the monitoring device 11 and the mobile terminal 12 can communicate with each other.

Figure 2:
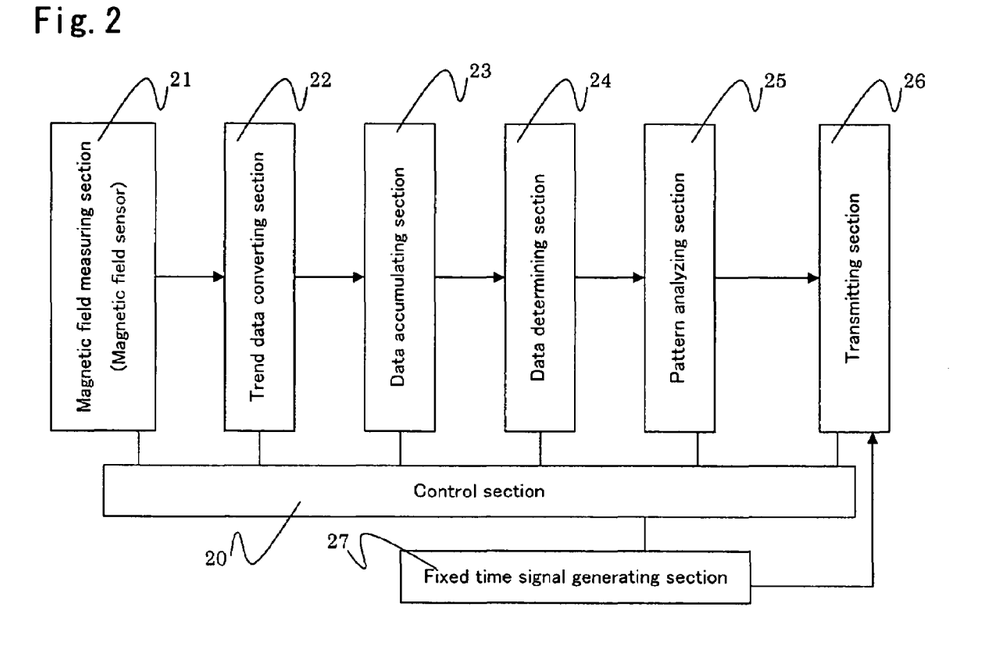
FIG. 2 is a block diagram illustrating a monitoring device 11.

FIG. 2 is a block diagram illustrating the monitoring device 11, and the monitoring device 11 according to the present invention includes an action potential measuring section 21 for measuring action potential generated when a human gets excited with a biomagnetic field sensor, a trend data converting section 22 for converting the action potential to time-series data, a data accumulating section 23 for serially accumulating the trend data, a data determining section 24 for determining whether accumulated data is normal or abnormal, a pattern analyzing section 25 for make analysis to determine whether a group of trend data concerning action potential determined as abnormal by the data determining section 24, a transmitting section 26 for transmitting a signal classifying and indicating a degree of abnormality determined as abnormal by the pattern analyzing section 25 to the mobile terminal 12, a fixed time signal generating section 27 for generating a connection confirmation signal irrespective of a result of determination by the pattern analyzing section 25, and a control section 20 for controlling each of the sections. Operations of the monitoring device 11 are described later.

Figure 3:
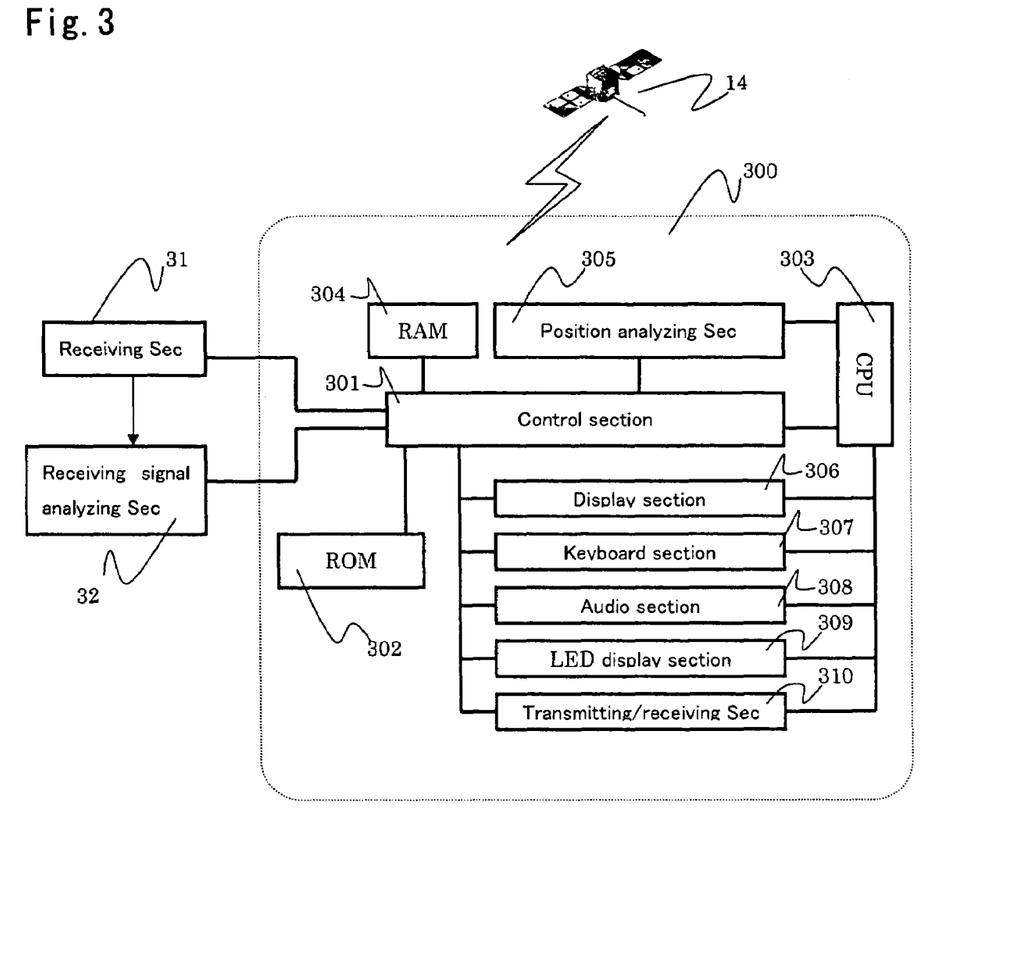
FIG. 3 is a block diagram illustrating a mobile terminal 12 as a medium for reporting abnormality.

FIG. 3 is a block diagram illustrating the mobile terminal 12 which is a medium for reporting abnormality in the object person 10 for monitoring. Shown in an area 300 surrounded by a dotted line are blocks in which general mobile terminal is ordinarily provided, and the blocks include a control section 301, a ROM 302, a CPU 303, a RAM 304, a position analyzing section 305, a display section 306, a keyboard section 307, an audio section 308, an LED display section 309, and a transmitting/receiving section 310.

The mobile terminal 12 according to the present invention includes, in addition to the blocks generally provided in the ordinary mobile terminal, a receiving section 31 for receiving an abnormal data signal transmitted from the monitoring device 11, and a received signal analyzing section 32 analyzing the abnormal data signal and reporting a result of analysis to the control section 301. A control program relating, for instance, to a method of starting the mobile terminal 12 according to the present invention is stored in the ROM 302 or in the RAM 304.

Figure 4:
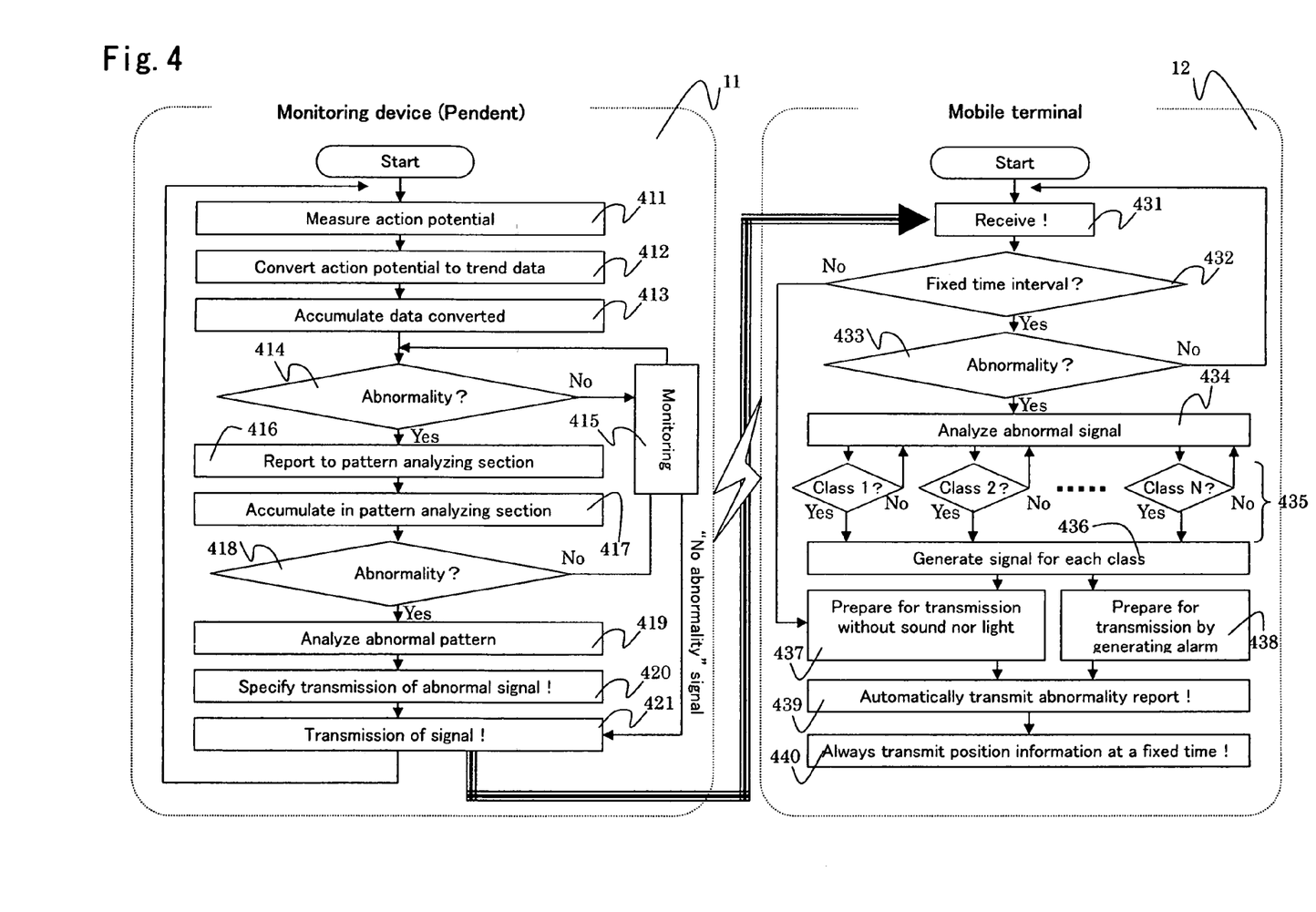
FIG. 4 is a flow chart illustrating a series of operations performed by the monitoring device 11 and the mobile terminal 12.

Next, description is provided for a flow of operations for automatically reporting occurrence of emergency and also automatically transmitting positional information in the human body monitoring system configured with the monitoring device 11 and the mobile terminal 12 with reference to FIG. 4. The first is a flow of operations from analysis of abnormality in the object person 10 to report of a result of the analysis to the mobile terminal 12 in the monitoring device 11.

The monitoring device 11 always executes measurement (step 411) action potentials with the action potential measuring section 21. The measured action potential is subjected to data conversion (step 412) by the trend data converting section 22 and is converted to time-series data. The data is accumulated (step 413) in the data accumulating section 23. The accumulated action potential trend data is subjected to determination (step 414) by the data determining section 24 for checking whether the data is normal or abnormal, and when it is determined that the data is normal, reporting is not performed and monitoring is continued (step 415). When it is determined by the data determining section 24 that the data is abnormal (414), the result is reported to the pattern analyzing section 25 (step 416), and the data is accumulated (step 417).

The determination as to whether the action potential trend data is normal or abnormal may not always be performed by converting the magnetic field values to a voltage or a current, and the determination may be performed by directly measuring the magnetic field values. When potential as a unit for measurement is to be measured, it is conceivable to measure action potentials in muscles. It is generally known that action potential in human muscles is 0 mV in the resting state, but goes up to around 100 mV when he or she gets excited. Furthermore it is also well known that a value of action potential varies according to a degree of excitation, that the potential drops according to a density of calcium ions generated in excitation, and that potential at the same level is generated to similar and successive stimuli with an even interval, and it is desirable to measure changes in the action potential by checking the parameters.

In the present invention, a biosensor capable of detection generation of various types of hormones may be used in place of the biomagnetic field sensor capable of measuring the action potential, but a non-contact type of biosensor as described above has not been known.

In the pattern analyzing section 25, the newly accumulated action potential trend data is compared to the action potential trend data accumulated up to the point of time for pattern analysis, and an importance degree of the abnormal state is determined (step 418). When it is determined that the emergent state is not so serious, reporting is not performed and monitoring is continued (step 415). When it is determined by the pattern analyzing section 25 that the data is abnormal, a degree of abnormality (step 419) is analyzed, and report data indicating a degree of seriousness is generated and transmitted for specification (step 420). The transmitting section 26 having received this signal sends the signal to the mobile terminal 12 for reporting (step 421).

Also a configuration is allowable in which the steps 416 to 418 are omitted and reporting data is sent, without performing pattern analysis, from the transmitting section 26 to the mobile terminal 12 only based on a result of trend analysis.

An operation flow in the mobile terminal 12 is described below.

The received signal analyzing section 32 in the mobile terminal 12 monitors whether the connection confirmation signal transmitted always or at a fixed time interval from the fixed time signal generating section 27 in the monitoring device 11 via the transmitting section 26 is received by the receiving section 31 (step 432). When it is determined that the signal is not received by the signal receiving section 31 at a fixed time interval (step 432), the received signal analyzing section 32 automatically reports the abnormality to a prespecified contact address or the management center 13.

Excluding the case where transmission of the connection confirmation signal is interrupted or stopped to indicate occurrence of any emergency, when the mobile terminal 11 receives a signal from the monitoring device 11 (step 431), the received signal analyzing section 32 determines whether the signal indicates any emergency or not. When it is determined that the signal does not indicate occurrence of emergency, the mobile terminal 11 waits for arrival of another incoming signal. When it is determined that the received signal indicates occurrence of any abnormality, the received signal analyzing section 32 analyzes the signal (step 434), and determines a degree of abnormality. The received signal analyzing section 32 decides a transmitting unit for automatically reporting the abnormality to a prespecified contact address or the management center 13 according to the degree of abnormality (step 436). When it is determined that the abnormality is serious, the report is automatically reported to the prespecified contact address or the management center 13 without generating any sound nor lighting (step 437). When it is determined that the abnormality is not so serious, the report is automatically transmitted (step 439) in the normal state (step 438). The reporting without generating any sound nor lighting means that the mobile terminal does not generate any sound and also the LED display section 309 or the display section 306 is not lit so that reporting is made without being noticed by the perpetrator or the like.

Furthermore, after reporting occurrence of abnormality, irrespective of a degree of the abnormality, a signal indicating the current position of the mobile terminal 12 is continuously transmitted at a fixed time interval to inform the current position (step 440).

In the embodiment described above, the data accumulating section 23, the data determining section 24, and the pattern analyzing section 25 are provided in the monitoring device 11, but the functional sections may be provided in the received signal analyzing section 32 in the mobile terminal 12. In this case, the monitoring device 11 only measures action potential and transmits the measurement data, and a series of analyzing operation is performed by the mobile terminal 12.

The data accumulating section 23, the data determining section 24 and the pattern analyzing section 25 may be provided on a server in the management center 13. In this configuration, the monitoring device 11 measures action potential and transmits the data, and the mobile terminal 12 only confirms reception of the connection confirmation signal and relays the data signal. The analyzing operations described above are performed by the server in the management center 13.

What is claimed is:

1. A human body monitoring system comprising a monitoring device carried by a person to be monitored and having a transmitting section and a mobile terminal carried by the person to be monitored and having a receiving section, the mobile terminal connected to the monitoring device through a wireless communication system using a weak electric wave and capable of reporting, based on an abnormal data signal received by the mobile terminal from the monitoring device, the abnormal signal and information concerning a position where an emergency occurs to a prespecified contact address or a management center, wherein the monitoring device has a non-contact biomagnetic field measuring sensor, monitors trends in action potentials in the target person for monitoring with the sensor, and transmits the abnormal data signal to the mobile terminal.

2. The human body monitoring system according to claim 1, wherein a coverage distance of the weak electric wave is within 10 meters.

3. The human body monitoring system according to claim 1, wherein the monitoring device comprises an action potential measuring section comprising the biomagnetic field measuring sensor; a trend data converting section for converting information concerning the action potentials to digital data in the chronological order; a data accumulating section for serially accumulating the trend data; a data determining section for determining whether accumulated data is normal or abnormal; a pattern analyzing section for determining whether a continuous pattern of action potential trend data groups determined as abnormal by the data determining section is abnormal or not; a transmitting section for transmitting a signal classifying and indicating a degree of abnormality determined as abnormal by the pattern analyzing section to the mobile terminal; a fixed time signal generating section for generating a connection confirmation signal irrespective of a result of determination by the pattern analyzing section; and a control section for controlling each of the sections above.

4. The human body monitoring system according to claim 1, wherein the monitoring device comprises an action potential measuring section comprising the biomagnetic field measuring sensor; a trend data converting section for converting information concerning the action potentials to digital data in the chronological order; a data accumulating section for serially accumulating the trend data; a data determining section for determining whether accumulated data is normal or abnormal; a transmitting section for transmitting a signal classifying and indicating a degree of abnormality determined as abnormal by the data determining section to the mobile terminal; a fixed time signal generating section for generating a connection confirmation signal irrespective of a result of determination by the data determining section; and a control section for controlling each of the sections above.

5. The human body monitoring system according to claim 1, wherein the mobile terminal comprises a received signal analyzing section for analyzing an abnormal data signal received by the receiving section and notifying a result of the analysis to a control section of the mobile terminal.

* * * * *